United States Patent [19]

Dahms

[11] Patent Number: 4,861,650

[45] Date of Patent: Aug. 29, 1989

[54] POLYIMIDE LAMINATES

[75] Inventor: Ronald H. Dahms, Springfield, Mass.

[73] Assignee: Monsanto Company, St. Louis, Mo.

[21] Appl. No.: 284,016

[22] Filed: Dec. 14, 1988

Related U.S. Application Data

[63] Continuation-in-part of Ser. No. 944,158, Dec. 18, 1986, Pat. No. 4,816,512.

[51] Int. Cl.$^4$ .................... B32B 27/12; B32B 27/18; B32B 27/28
[52] U.S. Cl. .................... 428/251; 156/307.4; 156/307.5; 156/307.7; 428/252; 428/272; 428/273; 428/285; 428/287; 428/288; 428/290; 428/408; 428/435; 428/458; 428/473.5; 428/542.8; 428/901
[58] Field of Search ............... 156/307.4, 307.5, 307.7; 428/251, 252, 272, 273, 285, 287, 288, 290, 408, 435, 458

[56] References Cited

U.S. PATENT DOCUMENTS 4,816,512 3/1989 Dahms ............................... 524/606

Primary Examiner—James C. Cannon
Attorney, Agent, or Firm—R. Bruce Blance; Thomas E. Kelley; William J. Farrington

[57] ABSTRACT

Polyimide laminates are prepared from solutions of maleimide resins comprising a mixture of maleimides and maleamic acids, e.g., greater than about 45% bis-maleimide and up to about 40% bis-maleamic acid and a stabilizing amount of polyamine. The bismaleimide is preferably derived from 2,2-bis[4-(4-aminophenoxy)-phenyl] propane.

18 Claims, No Drawings

POLYIMIDE LAMINATES

This application is a continuation-in-part of Application. Ser. No. 944,158, filed Dec. 18, 1986, and now Pat. No. 4,816,512.

This invention relates to prepregs and laminates based on polyimides and in particular it relates to prepregs and laminates prepared from a bismaleimide-polyamine composition.

BACKGROUND OF THE INVENTION

Bisimide resins, e.g. bismaleimide resins, are advantageously used in providing resin matrix composites, e.g. glass or carbon fiber reinforced laminates, to achieve enhanced properties such as greater thermal stability and lower moisture sensitivity than is possible with other composites, e.g. composites based on epoxy or other resins. A common bisimide, i.e. bis(4-maleimidophenyl)methane, exhibits poor solubility in many organic solvents of choice. Its use in commercial manufacture of laminates is facilitated by dissolving the bisimide in N-methyl pyrrolidone (not a preferred solvent) and by chain extension by Michael addition reaction with diamines.

Nishikawa, et al., disclose in U.S. Patent 4,460,783 that certain aromatic ether bismaleimide compounds such as bis(malimidophenoxyphenyl) propane and the like are highly soluble in desirable solvents such as acetone, toluene, methyl ethyl ketone and the like. See also Harvey et al in "New Aromatic-Ether Bismaleimide Matrix Resins", *ANTEC '86*, page 1311.

It has been discovered that the solubility of such aromatic ether bismaleimides is dependent on the presence of a considerable amount of acid group-containing precursor, i.e. having terminal amic acid groups not converted to the terminal imide group. Such acidic precursor material advantageously renders the bisimide soluble. However the terminal acid groups will tend to liberate water from ring closing imidization during cure of such resin. Such water will be vaporized during normal curing conditions and may tend to generate voids or blisters in fabricated articles such as laminates. Such water liberation is tolerable in some fabrication practices that can accommodate liberated water. However, in other applications it is especially desirable that bisimide resins cure with minimal liberation of water.

An object of this invention is to provide prepregs and laminates from soluble maleimide resin comprising predominately bismaleimide compound and low but solubilizing levels of an acid-containing precursor.

Another object is to provide prepregs and laminates from concentrated solutions of such resin compositions in common organic solvents containing sufficient polyamine to maintain the bismaleimide component in solution.

Still another object is to provide such resins and solutions for use in the preparation of prepregs and laminates that rapidly form a viscous thermoplastic resin minimizing flow from the reinforced matrix even during severe curing conditions, e.g. high pressure.

SUMMARY OF THE INVENTION

This invention provides prepregs and laminates from soluble compositions of bismaleimide resins which comprise a mixture of maleimides and maleamic acids. Solutions of bismaleimides exhibiting enhanced stability are achieved by providing a minor amount of polyamine, e.g. up to about the equivalent amount of maleamic acid of the composition. Resins that become rapidly viscous upon heating are advantageously provided by utilizing polyamines having secondary amine groups. This invention also is directed to methods of making such prepregs and laminates.

DETAILED DESCRIPTION OF THE INVENTION

Compositions used in making the prepregs and laminates of this invention are soluble in common organic solvents such as acetone, methyl ethyl ketone, toluene and the like and comprise a mixture of maleimides and maleamic acids of the formula:

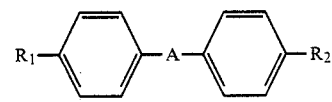

where A is

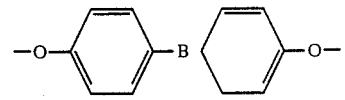

or —B— where B is —O—, —SO$_2$—, —CHCH$_3$—, —CH$_2$—, —CO—, —C(CH$_3$)$_2$—, —C(CF$_3$)$_2$— or a carbon-carbon bond, where R$_1$ and R$_2$ are independently the maleamic acid group, —NHCOCH=CH-COOH, or the maleimide group

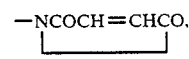

where R$_1$ and R$_2$ are the same providing a mixture of about 45 to 85 parts by weight bismaleimide and about 1 to 40 parts by weight bismaleamic acid and are different thereby providing a balance of maleimide-maleamic acid. In certain preferred embodiments of this invention A is

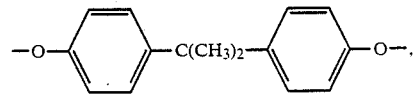

providing maleimides and maleamic acid compounds derived from bis(aminophenoxyphenyl) propane.

The mixtures of maleimides and maleamic acids used in this invention can be prepared from diamine precursors by methods generally known in the art and disclosed, for instance, in U.S. Patents 3,562,223 and 4,460,783, both of which are incorporated herein by reference. The mixtures of maleimides and maleamic acids which desirably are predominately the bismaleimide with minor amounts of the bismaleamic acid can be prepared by condensation reaction of maleic anhydride with a diamine of the formula

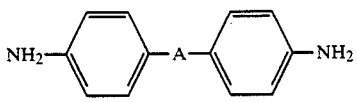

where A is as defined above. The bismaleamic acid product can generally be obtained in substantially pure quantities, e.g. at least about 90% bismaleamic acid or higher, say at least about 98% purity. The maleimides can be formed from the bismaleamic acid precursor by ring closure imidization resulting in the liberation of water. This ring closure is desirably effected in the presence of an acid anhydride dehydrating agent such as acetic anhydride, a tertiary amine ring closing agent such as triethylamine, and a metal acetate catalyst such as nickel acetate. The ring closing reaction is carried out to provide a mixture comprising about 45 to 85 parts by weight of the bismaleamide, and as little as 1 to about 40 parts by weight of the bismaleamic acid precursor. In certain embodiments the mixture preferably comprises about 50 to 80 parts bismaleimide and less than about 20 parts bismaleamic acid. More preferably, other embodiments comprise about 60 to 80 parts bismaleimide and less than about 10 parts bismaleamic acid. The remainder of 100 parts by weight of the mixture will generally comprise the partially imidized intermediate having both maleimide and maleamic acid terminal groups. Preferably the ring closing reaction is carried out under conditions mild enough to prevent the formation of substantial amounts of higher molecular weight oligomers.

Although purified bismaleimides and bismaleamic acids generally tend to be insoluble in solvents such as acetone, methyl ethyl ketone and toluene, compositions comprising mixtures of maleimides and maleamic acids useful in this invention have been found to be surprisingly soluble in such solvents.

Solutions of maleimide resin used in this invention to provide matrix composites, often desirably comprise from about 40 to about 70 percent solids of the maleimide-maleamic acid resin. Useful resin solutions will generally have a viscosity between 50 and 500 centipoise, although process requirements may require viscosities outside of that range. In many cases it is especially desirable that such solutions have a viscosity between about 100 and 200 centipoise.

Such solutions can be provided by solvents which can be selected from the group consisting not only of acetone, methyl ethyl ketone, and toluene but also of methyl isobutyl ketone, tetrahydrofuran, dimethylformamide, dimethylacetamide, dimethylsulfoxide, N-methyl pyrrolidone, ethylene dichloride, and xylene and the like or a mixture of such solvents. In many cases, the solvent of choice will consist essentially of acetone.

When solutions are intended to be used within a short period of time (e.g. within minutes or even hours, of dissolution) solutions of such mixtures, say up to about 50% by weight or higher can be obtained. However, in many cases, especially with relatively high concentrations of such mixtures, e.g. at least about 50% by weight, the bismaleimide component of the solution tends to separate over time from the solution in substantial quantities resulting in a solution containing disproportionately higher amounts of resin having maleamic acid terminal groups. Such maleamic acid terminal groups often undergo ring closing during cure with the result of liberation of water which may undesirably tend to form voids or blisters in composites and laminates.

It has been discovered that separation of bismaleimide compounds from solutions can be avoided by providing a minor amount of polyamine in the solutions of such mixtures of maleimides and maleamic acid. The amount of polyamine present in the solution to provide stability can be conveniently expressed in terms of equivalents of amine groups and maleamic acid groups, e.g. conveniently expressed in terms of the ratio of amine groups to maleamic acid groups. When the polyamine is present in solution such that the amount of amine groups is substantially less than the equivalent amount of maleamic acid groups, solubility may be enhanced but for a shorter period of time than when substantially the equivalent amounts are utilized. Moreover, when the polyamine is present such that the amount of amine groups is substantially greater than the equivalent amount of maleamic acid groups, stability will generally tend to be lessened, often with substantially increased viscosity of the solution. Such viscous solutions may tend to gel rapidly on heating, providing undesirable resin composites and laminates.

Considerable latitude can often be employed in determining such equivalence. In many cases it is advantageous to provide solutions where the ratio of amine groups to maleamic acid groups is from about 0.5 to about 4. To achieve exceptionally long stability, e.g. for days or weeks or more, without separation, e.g. by precipitation of a maleimide or maleamic acid component of the mixture, and to prevent an undue increase in viscosity, it is generally useful to provide polyamine so that the amount of amine groups is more nearly the equivalent of maleamic acid groups, e.g. where the ratio of amine groups to maleamic acid groups is about 0.8 to 2, and most preferably about 0.9 to 1.5.

The polyamine can comprise a diamine as used in preparing the bismaleimides of this invention, i.e. a diamine of the formula

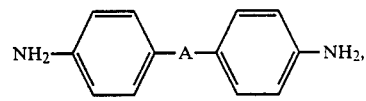

where A is described above or where the rings are saturated. Other suitable polyamines include diamines such as alkyl diamine, for instance diaminopropane, putrescine, cadaverine, hexamethylene diamine, and the like, polyalkylene oxide diamines of molecular weight in the range of 500 to 5000 such as polypropylene oxide diamines exemplified by Jeffamines available from Jefferson Chemical Company and triamines such as triaminononane and the like. It has been found that stable solutions that allow the resin to rapidly become viscous upon heating are achievable when the polyamine contains secondary amines, such as diethylenetriamine, triethylenetetramine, tetraethylenepentamine, pentaethylenehexamine, polyethyleneimine of molecular weight in the range of 500 to 5000 and amine-terminated rubber modifiers such as butadiene polymers and butadiene/acrylonitrile copolymers of molecular weight in the range of 500 to 5000 exemplified by Hycar Reactive Liquid Polymers available from B. F. Goodrich Co. Especially desirable resins that provide stable solutions but cause rapid increase in viscosity upon heating are provided with polyamines containing at least two secondary amine groups.

In one method of forming the resin matrix prepregs or composites and laminates of this invention, cloth such as glass or carbon fiber cloth (woven or nonwoven) is impregnated with a solution of this invention. Such impregnation can be conveniently carried out by dipping such cloth into a resin solution. Excess solution can be removed by passing the cloth through squeeze rolls. Solvent is removed in any convenient manner such as by heating the solution-impregnated cloth, e g. in an oven at a temperature often above the boiling point of the solvent. The length of time at elevated temperature is desirably short, e.g. less than about 10 minutes, but will be sufficiently long to remove solvent and advance or promote partial reaction of the resin to a coherent thermoplastic state (often called B-staging) providing a dry resin-impregnated cloth or prepreg. Such resin-impregnated cloth can then be provided in one or more layers which can be formed, e.g. thermoformed, and cured to provide a thermoset resin matrix composite structure by heating for an extended period of time, e.g. about an hour or more, at elevated temperatures say between about 150 and 300° C., preferably at least about 180° C. to about 250° C.

An effective amount of polyamine will also facilitate formation of dry resin-impregnated cloth. With low levels of polyamine, the resin will often remain molten, e.g. at temperatures of about 200° C., for undesirably long times, e.g. 20 minutes or more, even hours without reacting sufficiently to form a dry thermoplastic resin. When high levels of polyamine are utilized, e.g. substantially higher than about the equivalent amount of maleamic acid, the resin generally tends to rapidly gel upon heating, providing an undesirable foamy, brittle resin. Desirably the polyamine will assist in providing such dry thermoplastic resin in a short time, say less than about 10 minutes, preferably on the order of about 1 to 2 minutes. The time for formation of such dry thermoplastic resin is often correlated with "Dry Rubber Time", a predictive test defined more particularly herein in Example 3.

Some polyamines, e.g. diamines, allow for advantageous Dry Rubber Times, e.g. about 3 minutes or less, for solutions that are maintained for a short period of time, say about a day or so. However, when such solutions are maintained for longer times, e.g. about a week or more, Dry Rubber Times tend to increase to undesirable levels, e.g. about 5 minutes to 20 minutes or more. Advantageously, polyamines having secondary amine groups allow for short Dry Rubber Times even when solutions are maintained for several weeks. Accordingly, preferred aspects of the inventions disclosed herein comprise polyamines having secondary amine groups.

The following disclosure is provided to illustrate specific embodiments and aspects of the invention but does not imply any limitation of the scope of the invention.

EXAMPLE 1

This example serves to illustrate the preparation of a soluble composition of this invention comprising a mixture of maleimides and maleamic acids derived from bis(aminophenoxyphenyl) propane.

351 grams of maleic anhydride and 1,012 grams of acetone were heated to reflux temperature (about 63° C.) in a 5-liter reaction flask. A solution of 693 grams of 2,2-bis[4-(4-amino-phenoxy)phenyl]propane in 1,350 grams of acetone was metered into the refluxing solution over a period of 40 minutes. The reaction mixture was held at 30 minutes at reflux temperature to provide essentially 100 percent complete conversion to the diamic acid of 2,2-bis[4-(4-amino-phenoxy)phenyl]propane which precipitated as a yellow powder.

The following materials were added to the suspension of diamic acid in refluxing acetone: 495 grams of acetic anhydride, 3.375 grams of nickel acetate tetrahydrate, and 58.5 grams of triethylamine. The suspension was maintained at reflux temperature for about two hours then cooled to 50° C. The resulting clear solution was stirred into cold water yielding a precipitated yellow powder which was washed with water to remove solubles, filtered and dried in an air oven at 60° C. to constant weight. Analysis by high pressure liquid chromatography indicated that the powder comprised about 76 percent of the bismaleimide of 2,2-bis[4-(4-aminophenoxy)phenyl]propane and about 5 percent of the diamic acid; the balance of the powder is believed to be the half imidized intermediate having both maleimide and maleamic acid terminal groups.

EXAMPLE 2

This example serves to illustrate the preparation of a soluble composition of this invention comprising a mixture of maleimides and maleamic acids derived from methylene dianiline.

39.6 grams of methylene dianiline, 1.5 grams of benzyl dimethylamine, and 150 grams of acetone were cooled in a 500 cc flask to about 4° C. A solution of 43.1 grams of maleic anhydride in 200 grams of acetone was added over about a one hour period. The bismaleamic acid of methylene dianiline formed as a yellow precipitate as the mixture was stirred for an additional two hours at about 4° C. The bismaleamic acid was filtered, rinsed with acetone and dried at 65° C.

78.8 grams of the bismaleamic acid, 330 grams of acetic anhydride, 3.5 grams of calcium acetate monohydrate, and 400 grams of acetone were heated in a 1-liter flask for about one hour at reflux (about 60° C). Acetone was evaporated until the temperature rose to about 80° C. After continuing refluxing at about 80° C. for about 2 hours, the reaction mixture was poured into water resulting in a precipitate which was washed in water and filtered. Analysis by high pressure liquid chromatography indicated that the precipitate comprised about 49% of bismaleimide of methylene dianiline and about 34% of bismaleamic acid of methylene dianiline; the balance of the precipitate is believed to be the intermediate product having both maleimide and maleamic acid terminal groups.

A portion of the mixture was dried for one minute on a hot plate (about 167° C.) and dissolved in acetone at about 50% solids. After several days a small amount of acetone insoluble material precipitated from the 50% solution.

Another solution (about 75% solids) exhibited less stability with substantial amounts of acetone insoluble precipitate forming after about several hours.

The surprising solubility of a mixture of bismaleimide and bismaleamic acid of methylene dianiline is further indicated by comparison of solubilities of pure materials. As indicated above in the description of the formation, the solubility of the bismaleamic acid in acetone is extremely low. Moreover, commercially available bismaleimide of methylene dianiline (from Aldrich Chemical Company, purity 85%) has a solubility in acetone of less than about 10%.

EXAMPLE 3

This example serves to illustrate the stabilizing effect of polyamines on solutions of mixtures of maleimides and maleamic acids and the effect of polyamines on curing of such resins as indicated by Dry Rubber Time.

Dry Rubber Time provides an indication of relative cure rate especially for B-staging and, as specified herein, is a measurement of the time for a sample of resin solution to cure to a dry rubbery mass on a uniformly heated surface. More specifically, about a 1 cc sample of resin (dry or solution) is placed on a 200° C., uniformly-heated cure plate (Thermo-Electric Company, Cleveland, Ohio). The solvent rapidly evaporates as the solution is continuously spread with a spatula forming a molten resin. As the resin reacts to form polymer, thin strings can be pulled from the resin mass by the spatula. As the reaction continues, the resin mass forms into a coherent dry rubbery mass from which polymer strings cannot be drawn. The time at which strings are no longer formed is the "Dry Rubber Time". A Dry Rubber Time of "0" indicates almost immediate gelation of the solution.

The Dry Rubber Time for the resin mixture of maleimide and maleamic acids prepared in Example 1 was determined to be greater than three hours (about 10,000 seconds). That is, the test was discontinued after three hours when molten resin (at 200° C.) failed to form a coherent rubbery mass.

The addition of polyamine to a solution of such mixture provided substantially short Dry Rubber Times. Acetone solutions (about 60% solids) of the resin mixture of maleimides and maleamic acids and various polyamines were prepared as indicated in Table 1 by first dissolving the polyamine in acetone, then adding the resin mixture with agitation. The amount of polyamine is indicated by the ratio of amine groups to acid groups. For instance, the mixture of Example 1 was determined by titration to have 0.0362 equivalents of acid groups per 100 grams; and diaminoethane has 0.0333 equivalents of amine groups per gram (determined by dividing the number of amine groups, i.e. "2", by the molecular weight, i.e. "60"). Thus, adding 100 grams of the resin of Example 1 to a solution containing 0.94 grams of diaminoethane provides a solution where the ratio of amine groups to acid groups is determined to be about 0.86.

The results indicated in Table 1 indicate that polyamine can be advantageously added to solutions of soluble resin mixtures of maleimides and maleamic acids to provide exceptionally long stability of such solutions, e.g. up to three weeks and longer. Moreover the results indicate that certain polyamines can provide exceptionally short Dry Rubber Times, e.g. often less than about 5 minutes less, even after three weeks of storage.

EXAMPLE 4

This example serves to illustrate the preparation of dry resin-impregnated cloth or prepreg and cured laminates according to this invention.

65 grams of the resin mixture of bismaleimide and bismaleamic acids prepared in Example 1 was added to a solution of 0.975 grams of triethylene tetramine in 35 grams of acetone. (The ratio of amine groups to acid groups was about 1.13). The solution was used to saturate glass cloth. The solution saturated cloth was placed in an air oven (180° C.) for about 5 minutes resulting in a dry resin-impregnated cloth (about 38 percent by weight resin). A laminate was prepared by placing 8 sheets of resin-impregnated cloth between two sheets of copper having a density of two ounces per square foot and heating in a press for 2 hours at about 180° C.. and 3450 kPa (500 psi). The laminate was post cured at 220° C.. for 24 hours.

The laminate was evaluated in accordance with the procedures of MIL-P-13949F and determined to have the following properties:

| | |
|---|---|
| Water Absorption (23° C., 24 hours) | 0.4% |
| Dielectric Constant (at $10^6$ cps) | 3.5 |
| Dissipation Factor (at $10^6$ cps) | 0.01 |
| Copper Peel Strength | >60 kPa (9 psi) |

The laminate was also floated on molten solder (288° C..) for more than 10 minutes. The absence of blistering or delamination illustrate exceptional resistance to thermal stress.

While specific embodiments of the invention have been described, it should be apparent to those skilled in the art that various modifications thereof can be made without departing from the true spirit and scope of the invention. Accordingly, it is intended that the following claims cover all such modifications within the inventive concept.

TABLE 1

| | | Dry Rubber Time (seconds) | | | |
|---|---|---|---|---|---|
| Polyamine | R* | As made | 1 day | 6 days | 3 weeks |
| Control-No amine | — | >10,000 | — | — | — |
| 1,2-diaminoethane | 0.86 | — | 545 | — | — |
| 1,3-diaminopropane | 0.85 | — | 165 | 230 | 480 |
| " | 1.28 | — | 130 | 200 | 260 |
| 1,6-diaminohexane | 0.86 | 120 | 190 | 230 | 400 |
| " | 1.29 | 120 | 260 | — | 360 |
| Triaminononane | 0.87 | 110 | 170 | 450 | 540 |
| " | 1.20 | 80 | — | — | — |
| " | 1.73 | 0 | — | — | — |
| Polypropylene oxide diamine[1] | 0.86 | — | — | 1400 | — |
| Methylene dianiline | 0.85 | — | 170 | — | — |
| " | 1.71 | — | 100 | >1200 | — |
| " | 3.40 | — | 70 | >1200 | — |
| Bis(aminophenoxyphenyl) propane | 0.86 | — | 130 | >1200 | — |
| " | 1.72 | 70 | 100 | >1200 | — |
| Diethylene triamine | 1.05 | 80 | 90 | 225 | 420 |

TABLE 1-continued

| Polyamine | R* | Dry Rubber Time (seconds) | | | |
|---|---|---|---|---|---|
| | | As made | 1 day | 6 days | 3 weeks |
| " | 1.21 | — | 65 | — | — |
| " | 1.58 | — | 40 | — | — |
| " | 2.10 | — | 0 | — | — |
| Triethylene tetramine | 1.13 | 100 | 100 | 120 | 220 |
| " | 1.20 | — | 85 | — | — |
| " | 2.27 | — | 0 | — | — |
| Tetraethylene pentamine | 1.23 | 70 | 85 | 90 | 100 |
| " | 1.85 | — | 0 | — | — |
| Pentaethylene hexamine | 1.07 | 90 | — | — | — |
| " | 1.14 | 85 | — | — | — |
| " | 1.29 | 80 | 80 | 90 | 100 |
| " | 1.94 | — | 0 | — | — |
| Polyethylene imine[2] | (2.56 wt. %) | — | 55 | — | 55 |

[1]Jeffamine TM D230 (Jefferson Chemical Co.)
[2]Corcat TM P-18 (Virginia Chemicals Co.)
*R: ratio of amine groups to acid groups

What is claimed is:

1. A prepreg comprising a cloth impregnated with an organic solvent solution comprising a polyamine and a mixture of maleimide and maleamic acid compounds represented by the formula:

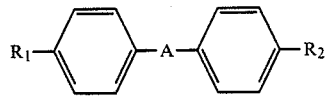

wherein —A— moiety is

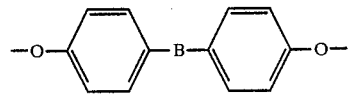

or —B—, and the B moiety is —O—, —SO$_2$—, —CHCH$_3$—, —CH$_2$—, —CO—, —C(CH$_3$)$_2$—, —C(CF$_3$)$_2$— or B is a carbon-carbon bond; where R$_1$ and R$_2$ are independently selected from the group consisting of the maleamic acid group, —NHCOCH=CHCOOH and the maleimide group,

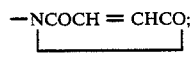

wherein the mixture comprises per 100 parts by weight of the mixture, from about 45 to parts by weight bismaleimide in which R$_1$ and R$_2$ are

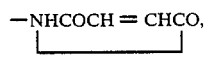

from about 1 to about 40 parts by weight of bismaleamic acid in which R$_1$ and R$_2$ are —NHCOCH=CHCOOH, and from about 0 to about 54 parts by weight of maleimide-maleamic acid in which R$_1$ is

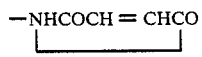

and R$_2$ is —NHCOCH=CHCOOH; and wherein the polyamine is present in sufficient amount to maintain in solution the bismaleimide component of the mixture of maleimide and maleamic acid compounds.

2. The prepreg of claim 1 wherein A is

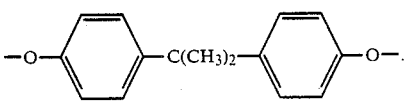

3. The prepreg of claim 2 wherein the organic solvent solution comprises about 40 percent by weight of the polyamine and the mixture of maleimide and maleamic acid compounds.

4. The prepreg of claim 2 wherein said polyamine is selected from the group consisting of diamino propane, diamino butane, diamino pentane, hexamethylene diamine, polypropylene oxide diamine, diethylene triamine, triethylene tetramine, tetraethylene pentamine, pentaethylene hexamine, triamino nonane, polyethylene imine, amine terminated polymers of butadiene and amine terminated copolymers of butadiene and acrylonitrile.

5. The prepreg of claim 3 wherein said polyamine comprises at least two primary amine groups.

6. The prepreg of claim 3 wherein said polyamine comprises at least two secondary amine groups.

7. The prepreg of claim 2 wherein the ratio of amine groups of the polyamine to maleamic acid groups of the mixture is in the range of about 0.5:1 to about 4:1.

8. The prepreg of claim 7 wherein the ratio is in the range of about 0.9 to about 1.

9. The prepreg of claim 1 advanced to the B-stage.

10. The prepreg of claim 2 advanced to the B-stage.

11. The prepreg of claim 4 advanced to the B-stage.

12. The prepreg of claim 7 advanced to the B-stage.

13. A laminate comprising at least two layers of the prepreg of claim 9.

14. A laminate comprising at least two layers of the prepreg of claim 10.

15. A laminate comprising at least two layers of the prepreg of claim 11.

16. A laminate comprising at least two layers of the prepreg of claim 12.

17. The laminate of claim 13 further comprising at least one outer layer of metal.

18. A method of preparing a laminate comprising
   (a) impregnating cloth with the organic solvent solution A1 of claim 1 and evaporating solvent therefrom, and advancing the resin to provide a B-staged resin-impregnated cloth under heating conditions, and
   (b) superposing at least two layers of said B-staged resin-impregnated cloth and heating them together under pressure at a temperature in the range of about 150 to about 300° C..

* * * * *

UNITED STATES PATENT AND TRADEMARK OFFICE
CERTIFICATE OF CORRECTION

PATENT NO. : 4,861,650
DATED : August 29, 1989
INVENTOR(S) : Ronald H. Dahms

It is certified that error appears in the above-identified patent and that said Letters Patent is hereby corrected as shown below:

At col. 1, line 28, delete "bis(malimidophenoxylphenyl) propane and insert therefor -- bis(maleimidophenoxyphenyl) propane -- .

At col. 10, line 45, delete "1" and insert therefor - - 1.5 - -.

At col. 10, line 62, delete "Al" and insert therefor - - comprising a polyamine and the mixture of maleimide and maleamic acid used to provide the prepreg - - .

Signed and Sealed this

Twelfth Day of November, 1991

*Attest:*

HARRY F. MANBECK, JR.

*Attesting Officer*      *Commissioner of Patents and Trademarks*